US007742931B2

(12) United States Patent
McElwain Miller

(10) Patent No.: US 7,742,931 B2
(45) Date of Patent: Jun. 22, 2010

(54) ORDER GENERATION SYSTEM AND USER INTERFACE SUITABLE FOR THE HEALTHCARE FIELD

(75) Inventor: Theresa McElwain Miller, Downingtown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2954 days.

(21) Appl. No.: 10/222,366

(22) Filed: Aug. 16, 2002

(65) Prior Publication Data
US 2003/0036925 A1 Feb. 20, 2003

Related U.S. Application Data

(60) Provisional application No. 60/313,667, filed on Aug. 20, 2001.

(51) Int. Cl.
*G06Q 50/00* (2006.01)
*G06F 19/00* (2006.01)
(52) U.S. Cl. .............................................. 705/2; 705/3
(58) Field of Classification Search ....................... 705/2
See application file for complete search history.

(56) References Cited

U.S. PATENT DOCUMENTS 5,737,539 A 4/1998 Edelson et al. .............. 395/203
5,786,816 A * 7/1998 Macrae et al. .............. 715/837
5,826,237 A * 10/1998 Macrae et al. ................. 705/2
5,850,221 A * 12/1998 Macrae et al. .............. 715/853
5,946,659 A * 8/1999 Lancelot et al. ................ 705/3
5,995,937 A * 11/1999 DeBusk et al. ................. 705/2
6,037,940 A * 3/2000 Schroeder et al. ........... 715/763
6,199,115 B1 3/2001 DiRienzo .................... 709/236
6,289,316 B1 * 9/2001 Aghili et al. ................... 705/3

OTHER PUBLICATIONS

Franklin, Modifiable Templates Facilitate Customization Of Physician Order Entry, 1998, Proc AMIA Symp, 315-9.*

* cited by examiner

*Primary Examiner*—Robert W Morgan
*Assistant Examiner*—Tran Nguyen
(74) *Attorney, Agent, or Firm*—Alexander J Burke

(57) ABSTRACT

An order generator for a healthcare information system and a corresponding method includes a user interface and a processor. The user interface includes an input device and a display. The input device receives input information related to format and content of an order form for a patient. The display presents the input information and output information related to the order form. The display includes an order template editor window and an order details window. The order template editor window permits a user to generate an order template responsive to receiving the input information. The order details window permits the user to generate the order form responsive to the generating the order template and responsive to receiving the input information. The processor generates the output information responsive to receiving the input information.

17 Claims, 12 Drawing Sheets

Order Template Editor Window
300

Healthcare Information System FIG. 1

Order Template Editor Window
300

Order Details Window
400

FIG. 4

- 402 — Order Details / Start
- Place New Order: Radiology
- Service being ordered:
- 404 — MRI
- 406 — How often? q4hrs
- 407 — Repeat...
- 408 — Duration: until d/c
- 410 — Start date/time: 09/01/2001 10:00 am
- 412 — Priority: routine
- 414 — If PRN, Condition:
- 416 — Reason for test
- 418 — Diagnoses for order: 123.5 xxxxxxxxxx
- 420 — Search...
- 422 — Remove
- 424 — Ordered by: Maxine Appleton, M.D.
- 426 — Copy result to:
- 428 — Call back #:
- 430 — Additional Clinical Info (accessed 1/1/2001):
  - LMP Date           10/05/2001
  - Pregnant?:         Yes
  - Pregnancy Indicator Date:  01/01/2001
  - # of Pregnancies:  1
  - Patient Condition: Fair
  - Allergic to Dye?   yes
  - Allergic to Latex? no
  - Other History Documentation   xxxxxxxxxxxx
- 432 — Additional documentation:
- 434 — x MRI Checklist / Edit...
- 436 — Additional directions:
- 438 — View: Lateral
- 440 — Body Site: Left Hand
- 442 — Modifiers: F1 LEFT HAND, SECOND DIGIT / FA LEFT HAND, THUMB
- 444 — Search...
- 446 — Remove
- 448 — Transport with? Oxygen / IV / Wheelchair / Monitor / Stretcher / Nurse / Physician
- 450 — History:
- 452 — Instructions to Cardiology:
- 454 — Status: Pending
- 456 — Entered by: Maxine Appleton, M.D.  on: 09/01/2001 10:00 am
- 458 — OK
- 460 — Close

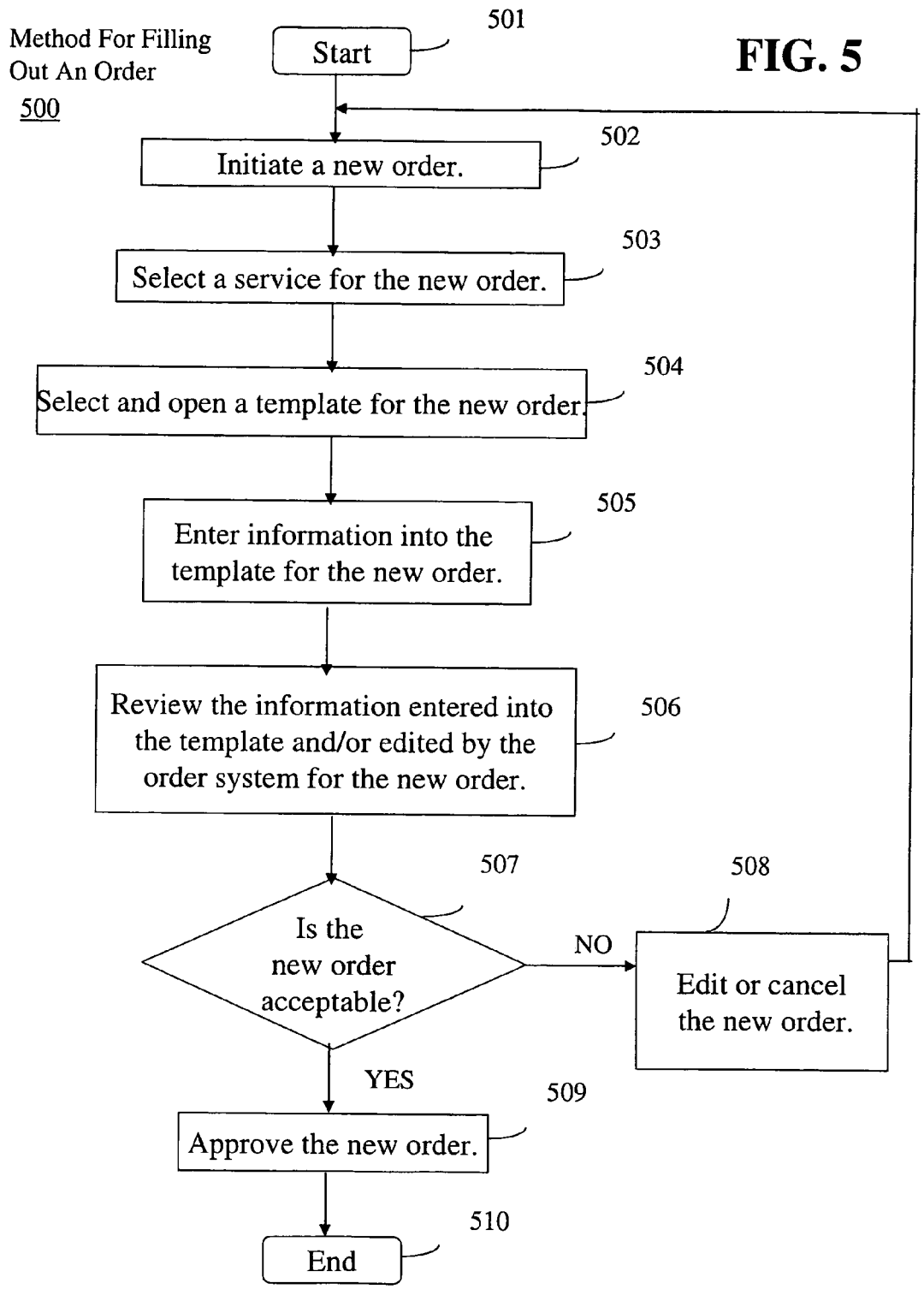

Order Template Tab Window
725

General Tab Window
727

FIG. 9

Order Placer Window
1100

Order Form Window
1200

ORDER GENERATION SYSTEM AND USER INTERFACE SUITABLE FOR THE HEALTHCARE FIELD

CROSS-REFERENCE TO RELATED APPLICATIONS

The present application is a non-provisional application of provisional application having Ser. No. 60/313,667 filed by Theresa McElwain Miller on Aug. 20, 2001.

FIELD OF THE INVENTION

The present invention generally relates to healthcare information systems. More particularly, the present invention relates to an order generator for a healthcare information system and a method therefor.

BACKGROUND OF THE INVENTION

Modern healthcare requires the concurrent provision of services by many health-care workers to many patients. In order to accomplish this, healthcare delivery has been organized into specialized departments such as, for example, nursing, laboratory, pharmacy, and radiology departments. Each department has responsibility for accomplishing its particular, often specialized, subset of tasks. Unfortunately, this has resulted in fragmented patient care and sub-optimal healthcare operations. A single healthcare process, such as the ordering and administration of a medication, sometimes requires the participation of multiple health-care workers that may be associated with multiple departments resulting in increased opportunities for error and delay.

Clinical and healthcare information systems have been computerized to help health care workers perform individual tasks. However, most systems typically have limited capability to manage a sequence of the individual tasks involved in healthcare processes. This is particularly true when the processes require the involvement of one or more health-care workers associated with one or more departments.

Some computerized systems include workflow management systems that are designed to manage complex processes, called workflows, which include multiple individual work steps, forming a sequence and schedule of tasks, performed by one or more workers associated with one or more departments. These systems permit customized configuration of the workflows, as well as continuous monitoring and management while the workflows are in progress. Preferably, these systems support configuration of the workflows at a local level where the workers implement the workflows.

Some computerized systems also have a user interface permitting workers to input information, such as via a keyboard or a touch screen, and receive output information, such via a display or recorded format on paper or a recording medium, related to the workflows. Workers use the user interface to perform tasks such as, for example, searching and reporting results, ordering goods and services, documenting clinical and nursing care, and capturing financial or operational data.

Usually, system administrators customize order forms for goods or services (e.g., test, medication, nursing activities, etc.) for a particular healthcare system. Present computerized systems require the administrator to create an order form for each type of or specific service. Typically, an order is hard coded in an order program that requires the services and time of a skilled programmer to make changes to create the customized order forms. Hence, the process for generating the order forms is complex and time consuming which directly affects the order form installation. Further, an end user, such as a doctor, typically needs to open a separate application to update relevant clinical information, such as patient assessment information, rather than being permitted to enter the update directly from an order form, which is time consuming and sometimes confusing.

In light of these and other deficiencies, it would be desirable for computerized systems to permit system administrators themselves to create order forms efficiently, without being a skilled programmer, to streamline the process of installing order forms for a healthcare information system. Preferably, the computerized system would generate the order forms using data stored in a master file. Such data driven order forms would be created as a by-product of performing maintenance of service definitions, thereby reducing installation time. The computerized system would also permit limited changes of the order format by end users, if desired. Further, integration of relevant clinical information (assessment, patient, etc.) on the order form also provides a streamlined order entry flow. Accordingly, there is a need for an improved order generator and corresponding method that would meet these and other desirable features of a healthcare information system.

SUMMARY OF THE INVENTION

An order generator for a healthcare information system and a corresponding method includes a user interface and a processor. The user interface includes an input device and a display. The input device receives input information related to format and content of an order form for a patient. The display presents the input information and output information related to the order form. The display includes an order template editor window and an order details window. The order template editor window permits a user to generate an order template responsive to receiving the input information. The order details window permits the user to generate the order form responsive to the generating the order template and responsive to receiving the input information. The processor generates the output information responsive to receiving the input information.

These and other aspects of the present invention are further described with reference to the following detailed description and the accompanying figures, wherein the same reference numbers are assigned to the same features or elements illustrated in different figures. Note that the figures may not be drawn to scale. Further, there may be other embodiments of the present invention explicitly or implicitly described in the specification that are not specifically illustrated in the figures and visa versa.

BRIEF DESCRIPTION OF THE DRAWINGS

FIG. 4 illustrates an order details window based on the order template editor window, shown in FIG. 3, in accordance with a preferred embodiment of the present invention.

FIG. 5 illustrates a method for filling out an order using the order generator, shown in FIG. 1, in accordance with a preferred embodiment of the present invention.

FIG. 9 illustrates a general tab window based on the service catalog window, shown in FIG. 7, in accordance with a preferred embodiment of the present invention.

DETAILED DESCRIPTION OF THE PREFERRED EMBODIMENTS

Figure 1:
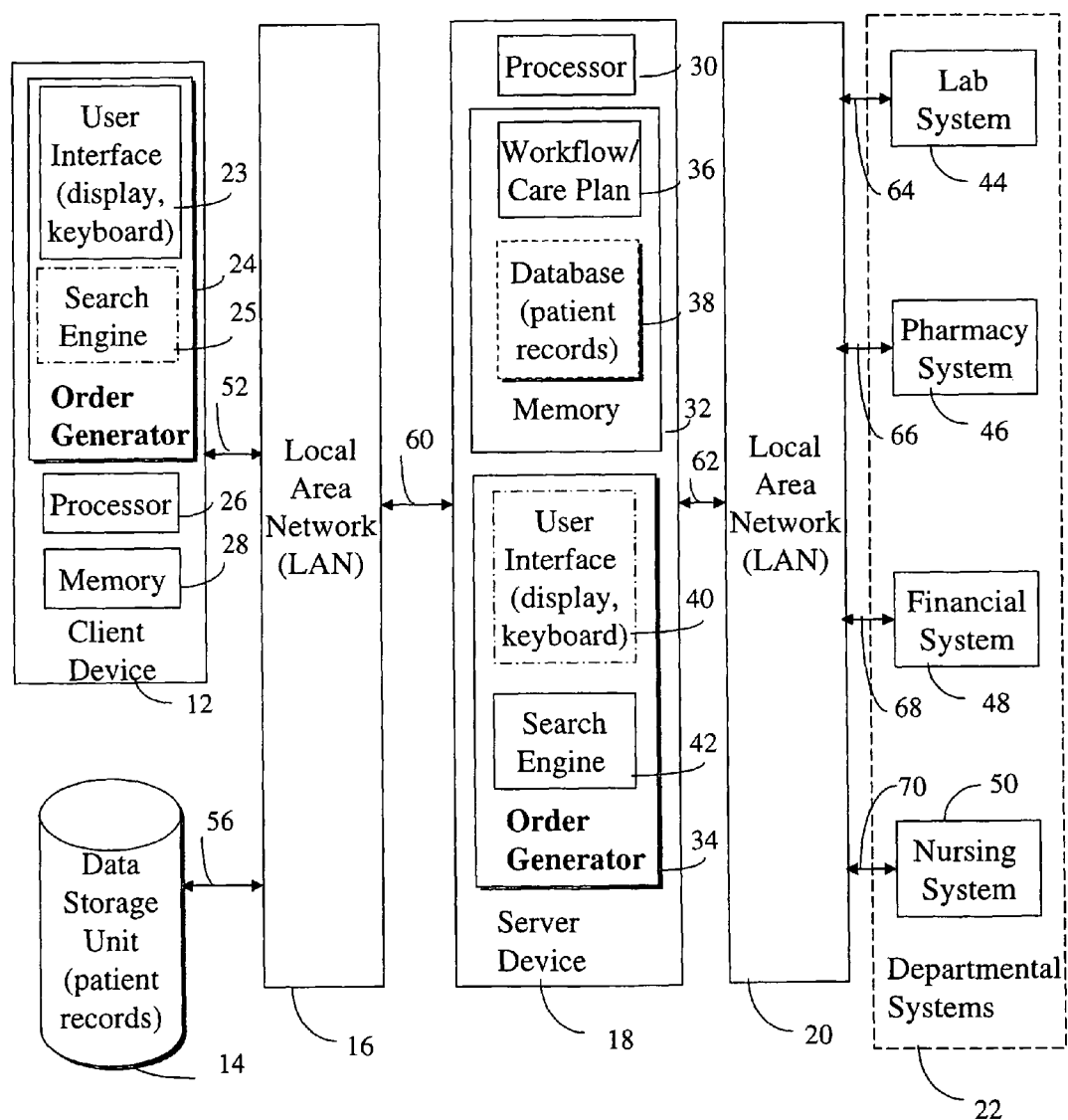
FIG. 1 illustrates a healthcare information system including an order generator, in accordance with a preferred embodiment of the present invention.

FIG. 1 illustrates a healthcare information system 10 including an order generator 24 and/or 34, in accordance with a preferred embodiment of the present invention. The healthcare information system 10 generally includes a client device 12, a data storage unit 14, a first local area network (LAN) 16, a server device 18, a second local area network (LAN) 20, and departmental systems 22. The healthcare information system 10 is intended for use by a healthcare provider that is responsible for monitoring the health and/or welfare of people in its care. Examples of healthcare providers include, without limitation, a hospital, a nursing home, an assisted living care arrangement, a home health care arrangement, a hospice arrangement, a critical care arrangement, a health care clinic, a physical therapy clinic, a chiropractic clinic, and a dental office. In the preferred embodiment of the present invention, the healthcare provider is a hospital. Examples of the people being serviced by the healthcare provider include, without limitation, a patient, a resident, and a client.

The client device 12 generally includes the order generator 24, a processor 26, and a memory unit 28. The order generator 24 preferably includes a user interface 23 and a search engine 25, but may also include the processor 26 and/or the memory unit 28. The client device 12 is preferably implemented as a personal computer. The processor 26 and the memory unit 28 are constructed and operate in a manner well known to those skilled in the art of the design of client devices. The order generator 24 may also include the processor 26 and/or the memory 28.

The user interface 23 in the client device 12 generally includes an input device that permits a user to input information into the client device 12 and an output device that permits a user to receive information from the client device 12. Preferably, the input device is a keyboard, but also may be a touch screen, a microphone with a voice recognition program, for example. Preferably, the output device is a display, but also may be a speaker, for example. The output device provides information to the user responsive to the input device receiving information from the user or responsive to other activity by the client device 12. For example, the display presents information responsive to the user entering information in the client device 12 via the keypad.

The search engine 25 in the client device 12 permits a user to search for specific information among a large amount of information. The search engine 25 is preferably implemented in software, but may also be implemented in hardware. The dashed lines around the search engine 25 represent that the location the search engine 25 in the client device 12 is an alternative location. In the preferred embodiment of the present invention, the search engine 42 is preferably located in the server device 18 to permit multiple users to have access to the same search engine 42 from multiple client devices.

The data storage unit 14 stores patient records, as well as other information for the hospital information system 10. Preferably, the data storage unit 14 is separate from the client device 12 to permit multiple users to have access to the patient records in the data storage unit 14 from multiple client devices. Preferably, the data storage unit 14 is separate from the server device 18 because of the physical size of the memory required to store all of the desired information. The data storage unit 14 may be implemented as read only memory (ROM), such as on a compact disk (CD) or on a hard drive, or a random access memory (RAM), and the like, as is well know to those skilled in the art of data storage units. Alternatively, the patient records may be stored in the database 38 in the memory unit 32 in the server device 18, as shown in dashed lines, in the memory unit 28 in the client device 12, or in memory units in the departmental systems 22, as the memory size becomes physically smaller, has increased capacity and becomes less expensive. An additional consideration would be the advantages and disadvantages of having the patient records stored in a single centralized memory unit or stored in several decentralized memory units among the data storage unit 14, the client device 12, the server device 18, and the departmental systems 22.

Patient records in the data storage unit 14 generally include any information related to a patient including, without limitation, biographical, financial, clinical, workflow, and care plan information. The patient records may be represented in a variety of file formats including, without limitation, text files such as documents, graphic files such as a graphical trace including, for example, an electrocardiogram (EKG) trace, an electrocardiogram (ECG) trace, and an electroencephalogram (EEG) trace, video files such as a still video image or a video image sequence, an audio file such as an audio sound or an audio segment, and visual files, such as a diagnostic image including, for example, a magnetic resonance image (MRI), an x-ray, a positive emission tomography (PET) scan, or a sonogram. The patient record is an organized collection of clinical information concerning one patient's relationship to a healthcare enterprise (e.g. region, hospital, clinic, or department). The patient record can narrowly be considered as a file cabinet or repository with divisions and indexing mechanisms. These divisions resemble a hierarchy with folders, documents and document components, or other objects representing collections of clinical elementary information. Such folder divisions include traditional classifications such as summaries, notes, investigations, orders, medications, correspondence, results, etc. Each individual information element and object resides in a home location in this structure. Revision history can be captured from within this home location.

The first local area network (LAN) 16 provides a communication network among the client device 12, the data storage unit 14, and the server device 18. The second local area network (LAN) 20 provides a communication network between the server device 18 and the departmental systems

22. The first LAN 16 and the second LAN 20 may be the same or different LANs, depending on the particular network configuration and the particular communication protocols implemented. Alternatively, one or both of the first LAN 16 and the second LAN 20 may be implemented as a wide area network (WAN).

The communication paths 52, 56, 60, 62, 64, 66, 68, and 70 permit the various elements, shown in FIG. 1, to communicate with the first LAN 16 or the second LAN 20. Each of the communication paths 52, 56, 60, 62, 64, 66, 68 and 70 are preferably adapted to use one or more data formats, otherwise called protocols, depending on the type and/or configuration of the various elements in the healthcare information systems 10. Examples of the information system data formats include, without limitation, an RS232 protocol, an Ethernet protocol, a Medical Interface Bus (MIB) compatible protocol, an Internet Protocol (I.P.) data format, a local area network (LAN) protocol, a wide area network (WAN) protocol, an IEEE bus compatible protocol, and a Health Level Seven (HL7) protocol.

The I.P. data format, otherwise called an I.P. protocol, uses IP addresses. Examples of the I.P. addresses include, without limitation, Transmission Control Protocol Internet Protocol (TCPIP) address, an I.P. address, a Universal Resource Locator (URL), and an electronic mail (Email) address. The communication paths 52, 56, 60, 62, 64, 66, 68, and 70 each may be formed as a wired or wireless (W/WL) connection. Preferably, the communication paths 52, 56, 60, 62, 64, 66, 68, and 70 are formed as a wired connection. In the case of a wired connection, the I.P. address is preferably assigned to a physical location of the termination point of the wire, otherwise called a jack. The jack is mounted in a fixed location near the location of the various elements. In the case of a wireless connection, I.P. addresses are preferably assigned to the various elements, since the various elements would be mobile. The wireless connection permits the person using the healthcare information system 10 to be mobile beyond the distance permitted with the wired connection.

The server device 18 generally includes a processor 30, a memory unit 32, and the order generator 34. The memory unit 32 includes a workflow and/or care plan 36 and a database 38 containing patient records. The order generator 34 preferably includes a user interface 40 and a search engine 42, but may also include the processor 30 and/or the memory unit 32. The server device 18 is preferably implemented as a personal computer or a workstation. As mentioned above, the database 38 provides an alternate location for storing the patient records, and the user interface 40 is an alternate interface for the user. Therefore, in the preferred embodiment of the present invention, the order generator includes the user interface 23 in the client device 12 and the search engine 42 in the server device 18. Alternatively, the order generator includes both the user interface 23 and the search engine 25 in the client device 12. Still alternatively, the order generator includes both the user interface 40 and the search engine 42 in the server device 18. Still alternatively, the order generator includes the user interface 40 in the server device 18 and the search engine 25 in the client device 12. The order generator 34 may also include the processor 30 and/or the memory 32.

The order generator 24 and/or 34 is a program that is used by users in a healthcare information system to define service information to drive the form and content of a patient's order to the user in a dynamic fashion. Specifically, the order generator 24 and/or 34 permits the user to vary the form and content of the patient's order responsive to the patient's medically responsible organization, type of service, subtype of service, and specific service, as well as other applicable criteria. Such form and content include, without limitation, independently or in any combination, the following: data presented on the order detail form including order and related information such as patient assessment, observation, patient, allergies, etc. that is needed to complete the order request (e.g., last menstrual period (LMP) and pregnancy indication are required for most radiology orders to be requested); defaults, allowable values, whether required or optional; labels, field formatting, free text or not free text; data information that is not on the detail form but is used for edit/validation; identification of whether a document like or data collection style is used as the appearance of the order detail form; and addition of additional organization specific data and types of orders that is not predefined by the order generator program's manufacturer.

Preferably, the order generator 24 and/or 34 dynamically creates the order form based on a master file definition by automatically placing the fields on the detail form based on an identified sequence. Further, the order generator 24 and/or 34 permits the user to pre-view and customizing the order form to make it prettier (e.g., frame captions, positioning, etc.).

The user may also define additional documentation templates required for certain types of orders that are not part of the basic required order and related clinical information, but are needed as support documentation. These document templates are accessible for quick access by the user from the order detail form.

During the order entry process, depending on the type, subtype of order, and specific service, the order generator 24 and/or 34 presents order and related clinical information to the user on the appropriate order detail form based on the information defined in the master files. Then, the user is presented with a list of related document templates for requisition details (e.g., MRI checklist for an MRI order) that the user can optionally select to fill out from the order entry process.

The departmental systems 22 are systems that need access to information or provide information related to the health and/or welfare of people in the care of the healthcare provider. Examples of the departmental systems 22 include, without limitation, a lab system 44, a pharmacy system 46, a financial system 48 and a nursing system 50, as shown in FIG. 1, but may also include a records system, a radiology system, an accounting system, a billing system, and any other system required or desired in a healthcare information system.

Figure 2:
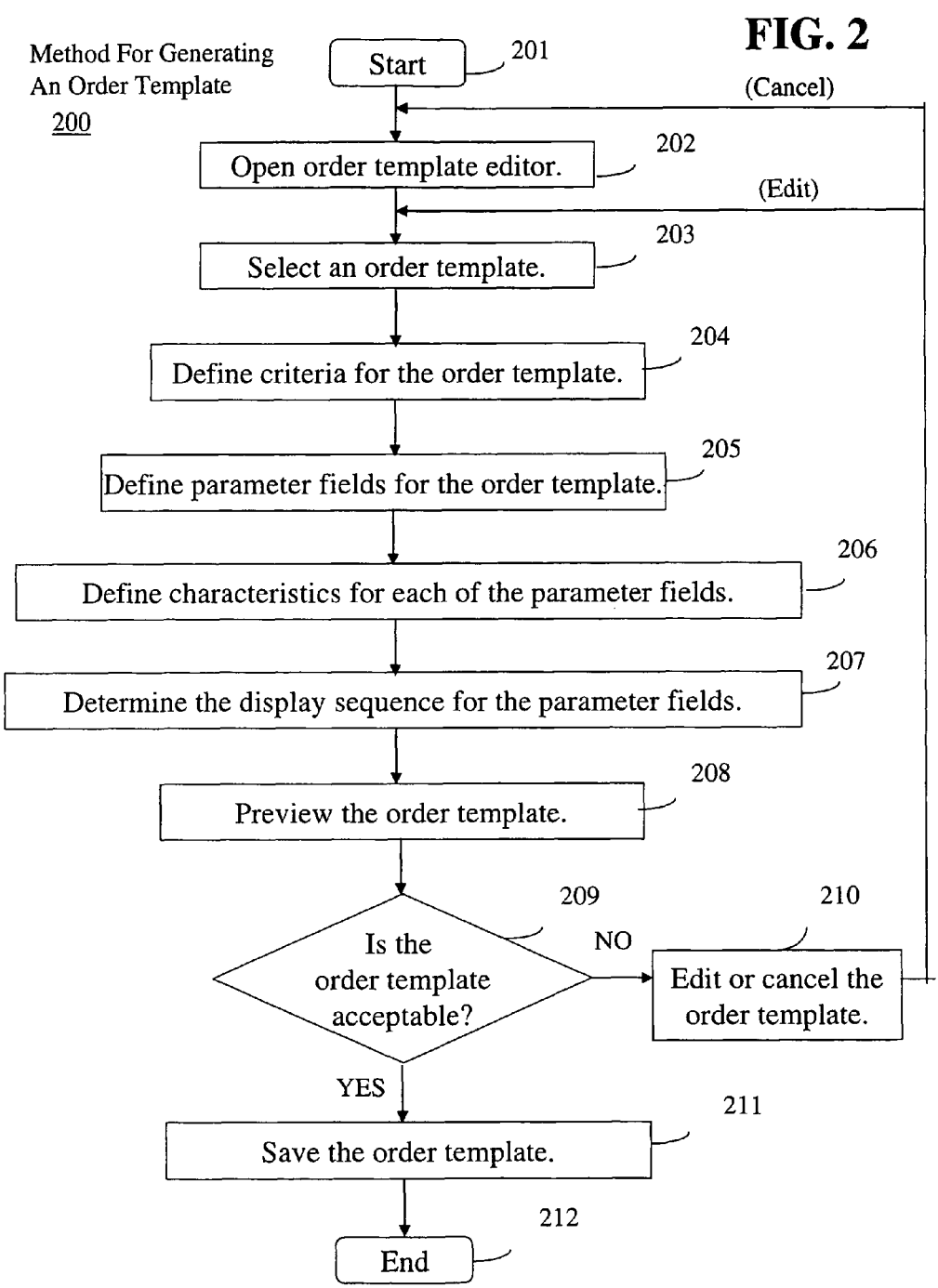
FIG. 2 illustrates a method for generating an order template using the order generator, shown in FIG. 1, in accordance with a preferred embodiment of the present invention.
Figure 3:
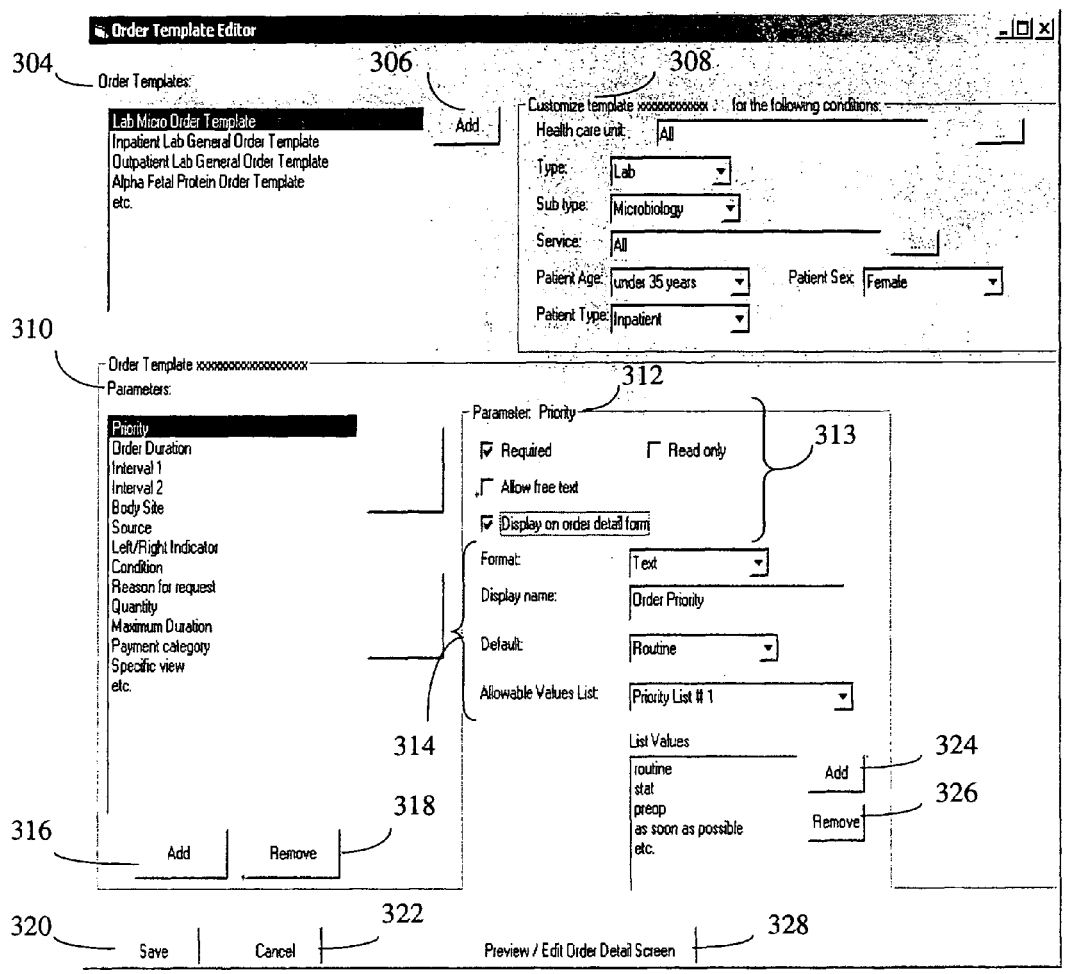
FIG. 3 illustrates an order template editor window using the method, shown in FIG. 2, in accordance with a preferred embodiment of the present invention.

Next, FIGS. 2, 3 and 4 are described together, wherein the steps of the method of FIG. 2 are described with reference to the features in the windows of FIGS. 3 and 4. FIG. 2 illustrates a method 200 for generating an order template using the order generator 24 and/or 34, shown in FIG. 1, in accordance with a preferred embodiment of the present invention. Although FIG. 2 is described from the perspective of the user, FIG. 2 also implicitly describes a corresponding method for generating the order template from the perspective of the order generator 24 and/or 34 because the order generator 24 and/or 34 receives inputs and provides outputs responsive to the user's actions. FIG. 2 is described for a user working in the capacity of a system administrator because FIG. 2 relates to the initial configuration or set up of the order templates. The description for FIG. 2 includes references and detailed descriptions for FIGS. 3 and 4, which provide examples of screen shots, otherwise called windows, which the order generator 24 and/or 34 provides to the display of the user interface 23 and/or 40.

In particular, FIG. 3 illustrates an order template editor window 300 using the method 200, shown in FIG. 2, in accordance with a preferred embodiment of the present invention. FIG. 3 generally includes an order template field 304; an order template add button 306; customized template fields 308 for criteria including, without limitation, health care unit, type, sub type, service, patient age, patient sex, and patient type fields; parameters 310 including add 316 and remove 318 buttons; characteristics of the parameter 312 including, without limitation, required, allow free text, display order detail form, and read only check boxes, and format, display name, default, checkboxes 313, fields 314, and list values add 324 and remove 326 buttons; and save 320, cancel 322, and preview 328 buttons.

In particular, FIG. 4 illustrates an order details window 400 based on the order template editor window 300, shown in FIG. 3, in accordance with a preferred embodiment of the present invention. FIG. 4 generally includes a place new order title 402, a service being offered field 404, a how often (i.e., frequency) field 406, a repeat button 407, a duration field 408, a start date/time field 410, a priority field 412, a pro re nata (PRN) (i.e., to give as needed) condition field 414, a reason for test field 416, a diagnoses for order field 418, a search button 420, a remove button 422, an ordered by field 424, a copy result to field 426, a call back number field 428, an additional clinical information field 430, an additional documentation field 432 field, an edit button 434, an additional directions area 436, a view field 438, a body site field 440, a modifier field 442, a search button 444, a remove button 446, a transport with field 448, a history field 450, an instruction field 452, a status field 454, entered by and date fields 456, an OK button 458, and a close button 460.

Referring to FIG. 2, with reference to FIGS. 3 and 4, the method 200 starts at step 201.

At step 202, the user opens the order template editor window 300, as shown in FIG. 3. Preferably, the user, a system administrator, accesses the order template editor window 300 via a menu item in the administrator's desktop, under catalog, and then under order template editor.

At step 203, the user selects appropriate order template 304. Preferably, the order templates 304 are grouped according to patient services. Preferably, the system administrator identifies a service (under customized template fields 308) in a service catalog that is accessible from the order template editor window 300 to view and select an existing template associated with a particular service. The service catalog defines service definitions for the enterprise and permits overrides for exception definitions at the healthcare unit level. The user may access the order template editor when defining the service. Preferably, the order template is defined at the healthcare unit criteria, under customized template fields 308.

The user may add a new order template or modify an existing order template. The order template permits the user to define information that is displayed, including, without limitation, fields that will be a default, fields that are required, allowable values that will be presented to the user, and other data that is needed to process the order that may not be presented on the display (e.g., may be needed for interface, charging, etc.).

By example, the service may include a blood bank service that would use an inpatient or an outpatient template depending on if the patient is processed as an inpatient or an outpatient, respectively. In this case, the order template includes an inpatient lab/blood bank order template, an outpatient lab/blood bank order template, an alpha fetal protein (AFP) service order template. In particular, the AFP service order template is used when AFP test is ordered. The outcome of a service specific order template cumulatively may add together the criteria of the general inpatient lab/blood bank order template and then overrides/adds additional criteria from the AFP service order template, or the user may define the AFP service order template as all inclusive. The user may copy the lab/blood bank order template to the AFP order template, and then modify the necessary data by removing and or adding ordering criteria to streamline this flow. In this case, only one template would be needed to implement the AFP order template. Either case meets the functional needs of the order generator.

By another example, the service may include a radiology service that uses a male radiology service order template or a female radiology order template depending on the patient's sex. The order template may be defined with a field context (e.g., wizard) to not show the LMP and pregnancy indicator when the patient is a male, or there may be two templates. Preferably, the wizard minimizes the amount of system administration setup using only one document. In a static document scenario, two different documents are created, one with LMP and pregnancy criteria for females and one without for males. In the order template driven document, the wizard hides the fields for male patients to permit the use of only one template. If a "Go-To-Logic" type wizard is used, the static document contains the fields with the LMP and pregnancy information. The order generator 24 and/or 34 displays these fields, but skips them when the patient is a male. In this case, only one document is needed.

At step 204, the user defines criteria 308 to customize the order template 304. The order generator 24 and/or 34 uses the criteria to determine which template to apply to the service based on the context that the service is ordered within. The criteria include, without limitation, healthcare unit level, type, subtype, service or orderable service set, patient age, patient sex, and whether the patient is being processed as an inpatient.

Design considerations for the criteria 308 include whether age, sex, and inpatient/outpatient are part of the criteria for the template or for the field. In some cases, this type of data may change for various order templates (e.g., pediatric versus adult detail form). In other cases, this type of data may stay the same but be hidden for some order templates (e.g., hiding the pregnancy field when the patient is male).

The criteria 308 permits the system administrator to define reusable templates for sets of services or for specific services. Preferably, the system 10 evaluates multiple templates to determine what criteria apply to a particular order template for the service (e.g., a service specific template would override the type/subtype template, or if the patient is an inpatient the inpatient lab type/subtype template would be used rather than the outpatient lab type/subtype template). Various design considerations may be made to the order generator 24 and/or 34 to accommodate these variations.

The order template editor window 300 provides fields with direct input or selection menus that display information to indicate whether to apply the criteria or not. Alternatively, checkboxes may be used for each criteria or a default checkbox to select all of the criteria. FIG. 3 shows the default all criteria under the healthcare unit field, as an example.

The criteria 308 may also include additional defaults provided by clinical decision support and other criteria. The other criteria may include, without limitation, service provider, device, user action/intent (e.g., admit/discharge, etc.), other patient factors, user, user group, role, subtype, type, specific service, inpatient/outpatient, healthcare unit, workflow function (e.g., charting, performing, ordering, scheduling, canceling), location, and the order template's ability to vary defaults within the package they are ordered in, which may be implemented by the user action.

At step 205, the user defines parameters 310 for the order template 304. The user may add and remove parameters using the add button 316 and the remove button 318, respectively. Preferably, the order generator 24 and/or 34 presents a list of order-focused parameters. The parameters 310 includes order data that may or may not show on the actual order form as well as relevant clinical information that users may want to include on the actual order form. Preferably, the system administrator predefines the parameters 310 for the health care organization in another program function at another time. The order generator 24 and/or 34 includes, without limitation, one or more of the following parameters 310. Preferably, the parameters 310, designated with and "R" below, are required by the application. Some of the parameters 310 may have multiple values that may be selected, as indicated below. Further, some of the parameters may have a search mechanism to permit searching. The search mechanism may be implemented as part of the document process of arranging the format of the order form in the order detail window 400 or part of the order template editor window 300. Order form detail related parameters, include, without limitation, include the following: priority 412, order duration/unit (multiple) 408, interval 1 (i.e., how often) 406, interval 2, body site (multiple) 440, source, left/right indicator, condition, reason for test (multiple) 416, quantity, maximum duration/unit, payment category, specific view (multiple) 438, service being ordered (R) 404, start date 410, start time 410, service requester person (R) (i.e., ordered by) (multiple, with search) 424, service requester healthcare unit (R) (with search), copy result to (multiple, with search) 426, call back # 428, comments, instructions to lab, instructions (general), guidelines, other reasons, history 450, instructions to cardiology 452, nurse collect, collected by (with search), collected on date, collected on time, order status (R) 454, activity status (R), entered by (R) 456, entered date (R) 456, entered time (R) 456, commenting level of result, service provider health care unit (R) 402 (with search), service provider person (with search), encounter, stop date, stop time, due date, due time, infectious indicator, consulting HCP/CHU (i.e., consult for ordering clinician or HCU or free text with search), requesting service (e.g., evaluate and treat, evaluate only), number of visits requested, and modifiers 444. Other parameters include, without limitation, the following: order id (R), planned (scheduled) date, planned (scheduled) time, signature, signed date, signed time, question, clinical information, result status, investigation date, result report date, result by, signature, result report, and conclusion. Relevant clinical information (e.g., patient, service, etc.) 430 include, without limitation, the following parameters: diagnoses for order (i.e., working diagnoses to associate to the order) (multiple, code and description, with search) 418, CPT modifiers (multiple items, such as code and description, with search), previous transfusion date, previous transfusion reactions (multiple), previous transfusion unit, number of pregnancies, additional documentation (i.e., a list of other documents templates (e.g., MRI checklist) that are accessible from order detail form to edit) (multiple) 432, transport with (e.g., multiple items, such as oxygen, iv, wheelchair, monitor, stretcher, nurse, physician) 448, is patient taking antibiotics?, name of drug, last dose date/time, height (in ft/in and m/cm), weight (in m/cm and lb/oz), problems (multiple, with search), LMP date, pregnant indicator, pregnancy indicator date, patient condition 414, allergy to dye, and allergic to latex. Further, the user may define other types of history documentation. Still further, other information may be included in the patient header. Preferably, the patient header information is separate and includes at least: patient name, age, sex, medical record number, date of birth, admission date, allergies, patient location, and isolation indicator. The user may also define the patient information, including, without limitation, the following: last name, first name, date of birth, patient id, and unit/ward.

At step 206, the user defines characteristics 312 for the selected parameter fields. The characteristics 312 may be in the form of checkboxes 313 or fields 314. The characteristics 312 include, without limitation, one or more of the following: required indicator, allow free text (i.e., manual data entry rather than selecting from a predefined list), read only, format (e.g., text, numeric, etc., if a customer added parameter), display on order detail form, display name (i.e., label for the window 300), default, allowable values list (allowable values lists may be reused across templates and fields), and list values (the list values permit the user to quickly create an allowable values list by adding or removing list values from the window 300 using the add button 324 and the remove button 326, respectively. Also permits users to view members of the allowable values list that is already associated with the order template. The values may be used across fields and order templates.)

At step 207, the user determines a display sequence 312 for the parameter fields 308. Preferably, the user selects a sequence of the parameters with up/down arrows (not shown in FIG. 3) to indicate the logical sequence of how the parameter information will be presented on the order form.

At step 208, the user previews 328 the order template 304. The order generator 24 and/or 34 presents the order form in the order detail window 400, as shown in FIG. 4, with the fields populated based on the parameter information and sequencing information defined on the order template editor window 300. Preferably, the order detail window 400 appears with the fields defaulted in the sequence as defined in the order template editor window 300. The order generator 24 and/or 34 uses allowable values of each element when presenting on the order detail window 400.

The user may move the fields within the order detail window 400 and may add text create a desired appearance to the order form. The user may also drag and drop new parameters from the list in the order detail window 400, add text labels for screen instructions, define frame titles for grouping information, and add text/instructions to the order detail window 400. Preferably, the user is not permitted to remove a required field. The order detail window 400 automatically includes the ok button 458 and the close button 460. Preferably, the order detail window 400 automatically includes the search button 420, the remove button 422, the edit button 434, the search button 444, and the remove button 446, but may be added by the user, if desired. The order generator 24 and/or 34 may permit the user to save the order form or automatically populate the order form, without manual intervention from the user. Alternatively, the order generator 24 and/or 34 presents the user with a form to select criteria to present in the order detail window 400. Preferably, this option would only be necessary when a static document includes the go-to-logic or when a template document is created. A separate document based on different criteria displays the selected document.

The order detail form permits the user to collect relevant clinical information in the detail form specific to the service. The user may also edit additional documents, such as a requisition detail document to collect additional details. The requisition template may be used when a lot of information or standard document of information is collected for a specific type of service (e.g., MRI checklist).

Figure 12:
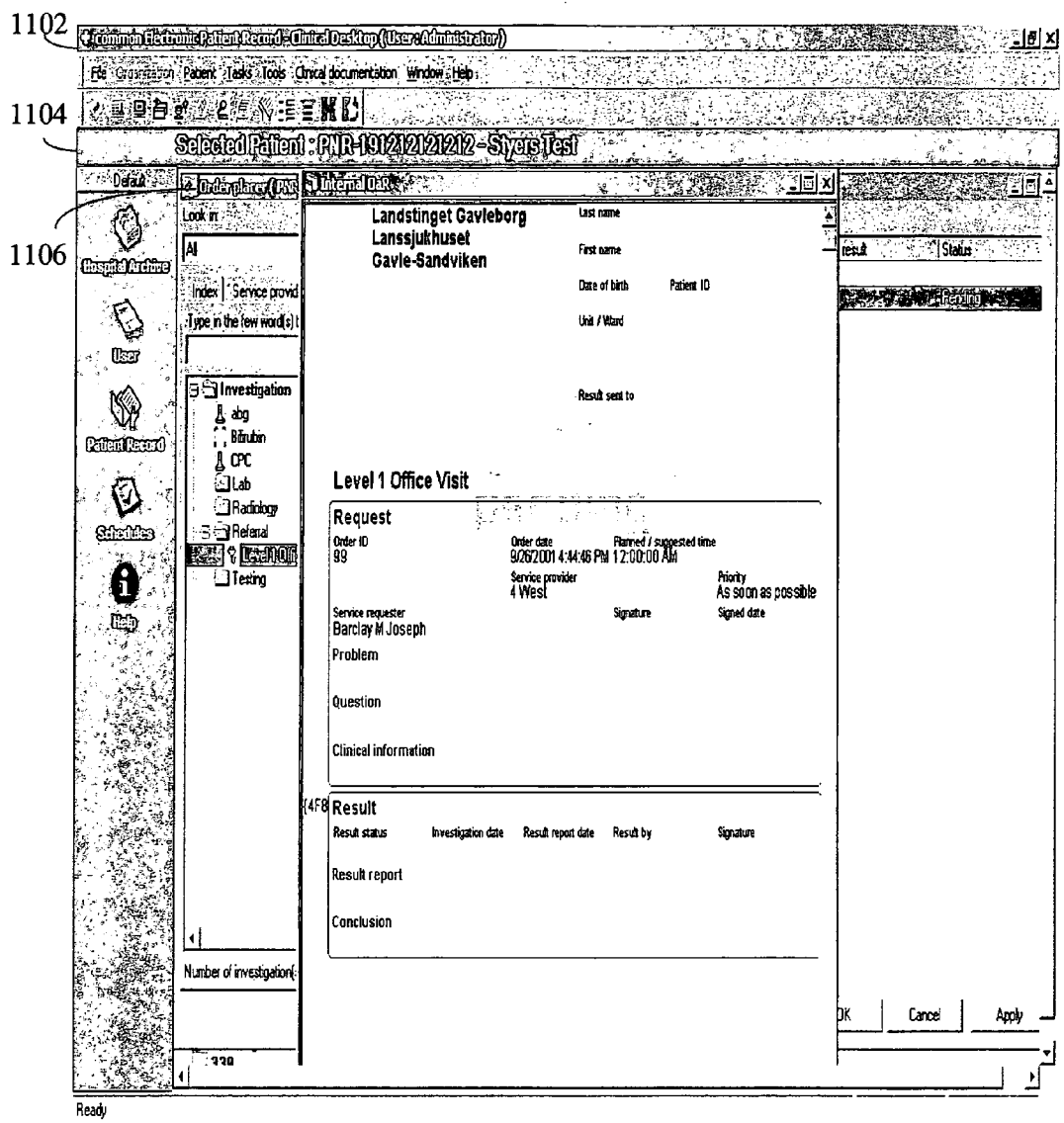
FIG. 12 illustrates an order form window using the order placer window, shown in FIG. 11, in accordance with a preferred embodiment of the present invention.

Preferably, when the order detail or the order requisition document is not defined, only the order detail window 400 appears to permit the user to collect relevant clinical information in the detail form specific to the service. Otherwise, when the order detail or the order requisition document is defined, the order detail document 1200, as shown in FIG. 12, associated with the service appears. Relevant clinical information also appears on this document, if it is defined. The user may also define a requisition template to display separately but most likely would define this information in the order detail document. The user can update order details in the order detail document 1200. The service provider can then update the results for the order in the order detail document 1200 later in the flow. Preferably, this process is used for specialist service request (SSR)/referral types of consult orders that are performed within the healthcare enterprise.

At step 209, the user determines whether the order template 304 is acceptable. If the order template 304 is not acceptable to the user, then the method 200 continues to step 210. Otherwise, if the order template 304 is acceptable to the user, then the method 200 continues to step 211.

Preferably, the user may add a user defined parameter and define its characteristics to present specific desired parameters. The defined parameter will be available for subsequent users and becomes part of the parameters listed in the order generator 24 and/or 34. The order generator 24 and/or 34 identifies the difference between user-defined parameters and manufacturer defined parameters.

Preferably, the system administrator defines relevant clinical information that needs to be viewed and collected specific to a service. This information will appear on the order detail form. This information is variable by the service requesting or responsible healthcare unit and for the specific service. The ability to associate these elements to a service is needed and to indicate what is required or optional for the service.

At step 210, the user edits the order template 304, or cancels the order template 304 by selecting the cancel button 322. When the user edits the order template 304, the method returns to step 203, wherein the user may change any information, including the format and/or content, in the order template editor window 300, as described above. When the user cancels the order template 304, the method returns to step 202, wherein the user must open the order template editor window 300.

At step 211, the user saves 320 the order template 304.

At step 212, the method 200 ends.

FIG. 5 illustrates a method 500 for filling out an order using the order generator, shown in FIG. 1, in accordance with a preferred embodiment of the present invention. Although FIG. 5 is described from the perspective of the user, FIG. 5 also implicitly describes a corresponding method for filling out an order from the perspective of the order generator 24 and/or 34 because the order generator 24 and/or 34 receives inputs and provides outputs responsive to the user's actions. Preferably, FIG. 5 is described for a user working in the capacity of an end user, such as a nurse, technician, or doctor, in the healthcare enterprise because FIG. 5 relates to the generating a new order using an order template already set up by the system administrator.

At step 501, the method starts.

At step 502, the user initiates a new order.

At step 503, the user selects a service for the new order. From a system point of view, the system 10 displays a summary "order as written" description, as a physician writes it, with an abbreviation of the parameters defaulted from the order template (e.g., Ampicillin 250 mg tid daily ×3 days) responsive to the user selecting the service for the new order. The summary description is built from the order template defaults. Examples of the summary descriptions are shown as reference 1112 in FIG. 11. The user then determines from the summary description whether any of the order information needs to be added or modified. If the order information needs to be added or modified, then the method continues to step 504. Otherwise, the method continues to step 506.

At step 504, the user selects and opens an order template for the new order.

At step 505, the user enters information into the order template for the new order.

At step 506, the user reviews the information entered into the order template and/or edited by the order generator 24 and/or 34 for the new order.

At step 507, the user determines whether the new order is acceptable. If the new order is not acceptable, the method continues to step 508. If the new order is acceptable, the method continues to step 509.

At step 508, the user edits or cancels the new order. After step 508, the method continues to step 502 to permit the user to edit the new order. Otherwise, the user cancels the new order.

At step 509, the user approves the new order.

At step 510, the method ends.

Figure 6:
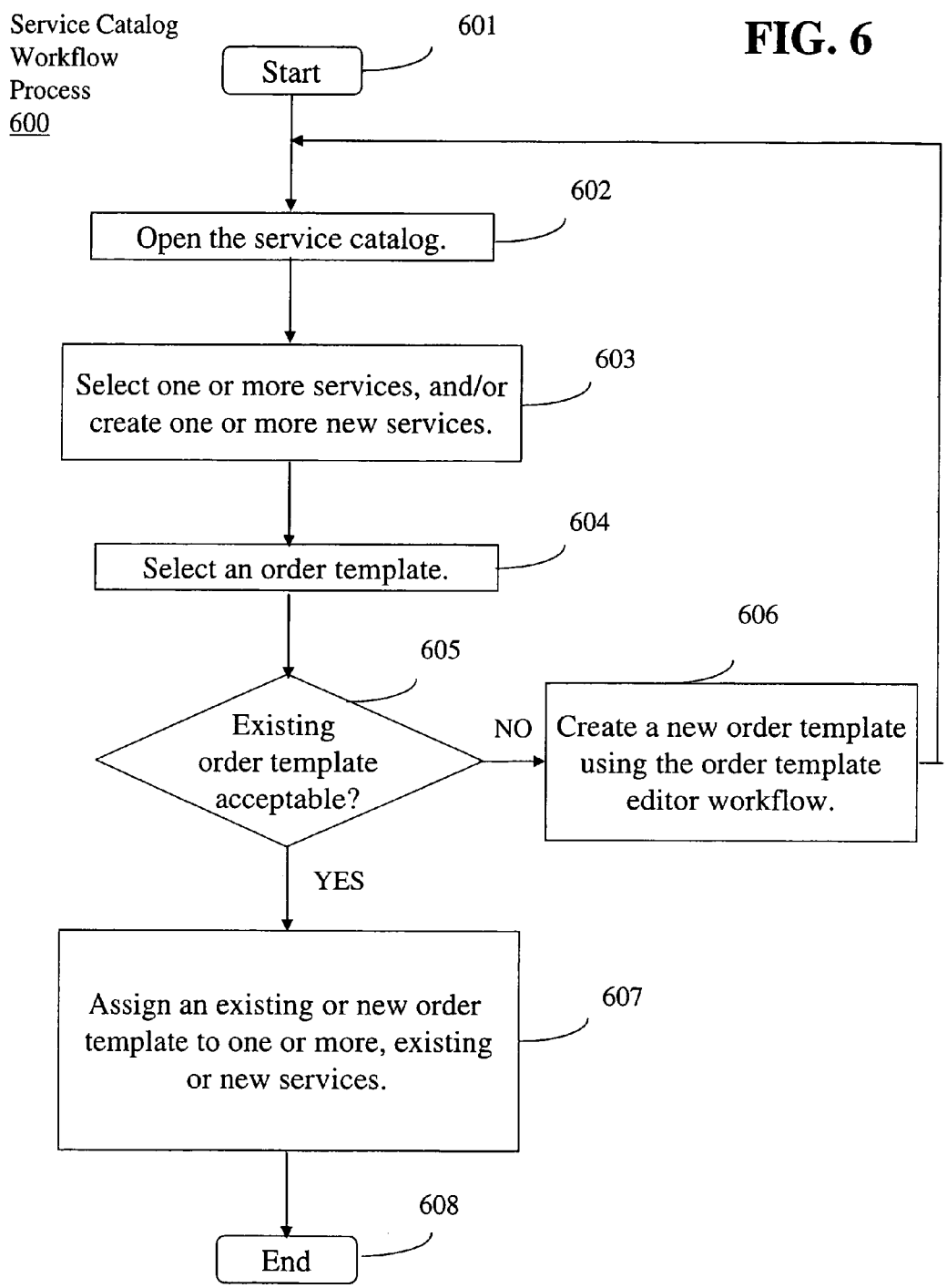
FIG. 6 illustrates a service catalog workflow process using the order generator, shown in FIG. 1, in accordance with a preferred embodiment of the present invention.

Next, FIGS. 6, 7, 8, 9 and 10 are described together, wherein the steps of the method of FIG. 6 are described with reference to the features in the windows shown in FIGS. 7, 8, 9 and 10. FIG. 6 illustrates a service catalog workflow process 600 using the order generator 24 and/or 34, shown in FIG. 1, in accordance with a preferred embodiment of the present invention. The service catalog workflow process 600 generally permits a user to select or create a service, view default order templates, and access the order template editor window 300 to either create a new order template or assign an existing or new order template to one or more, existing or new services. Although FIG. 6 is described from the perspective of the user, FIG. 6 also implicitly describes a corresponding service catalog workflow process 600 from the perspective of the order generator 24 and/or 34 because the order generator 24 and/or 34 receives inputs and provides outputs responsive to the user's actions. Preferably, FIG. 6 is described for a user working in the capacity of an end user, such as a nurse, technician, or doctor, or a system administrator in the healthcare enterprise because FIG. 6 relates to the generating a new order using an order template already set up by the system administrator or creating a new order template, respectively.

Figure 7:
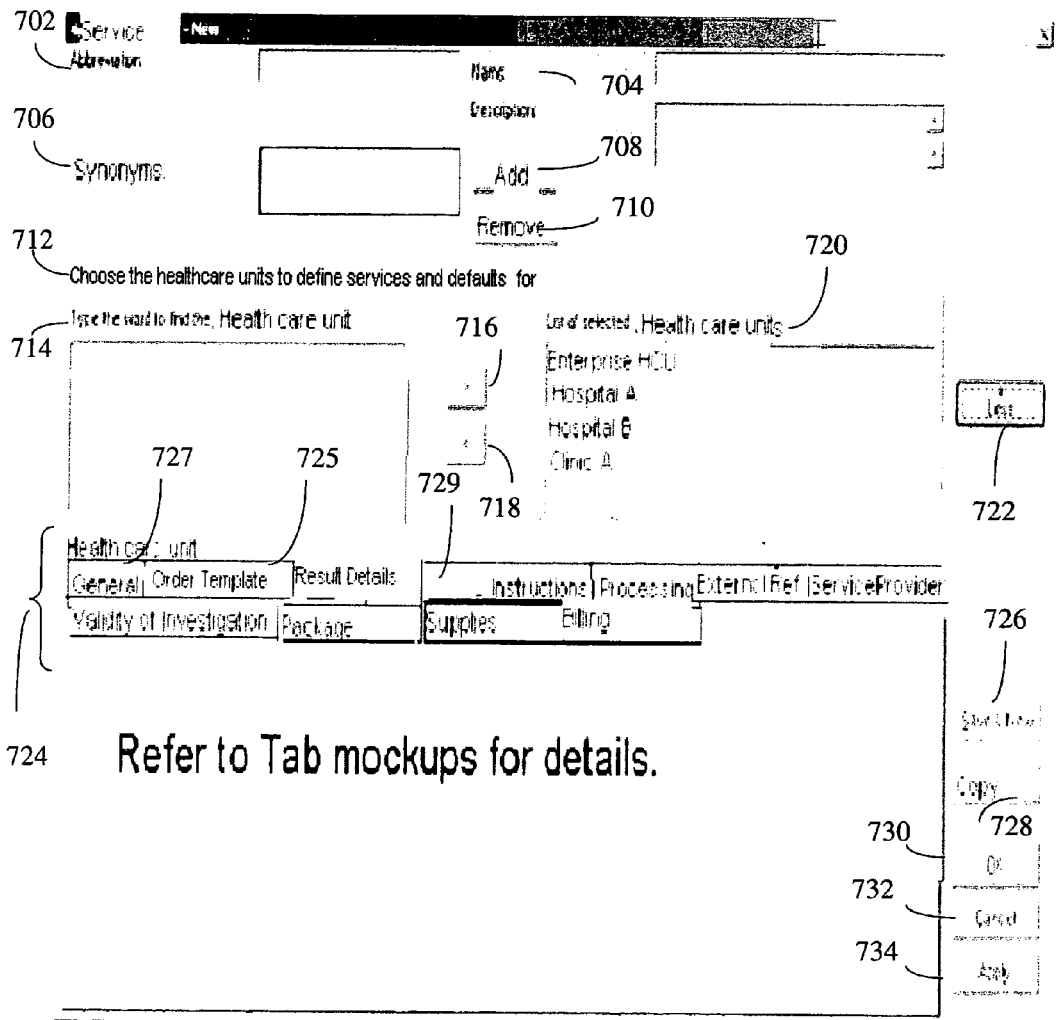
FIG. 7 illustrates a service catalog window using the method, shown in FIG. 6, in accordance with a preferred embodiment of the present invention.

FIG. 7 illustrates a service catalog window 700 using the method 600, shown in FIG. 6, in accordance with a preferred embodiment of the present invention. In particular, FIG. 7 generally includes an abbreviation field 702, a name field 704, a synonyms field 706, an add button 708, a remove button 710, a choose the healthcare units to define services and defaults for title 712, a type the word to find the healthcare unit field 714, a right arrow button 716, a left arrow button 718, a list selected healthcare field 720, a less button 722, several healthcare unit tabs 724 including a general tab 727, an order template tab 725, a result details tab, an instructions tab 729, a processing tab, an external tab, a reference tab, a service provider tab, a validity of investigation tab, a package tab, a supplies tag, and a billing tag, a save and new button 726, a copy button 728, an ok button 730, a cancel button 732, and an apply button 734.

Figure 8:
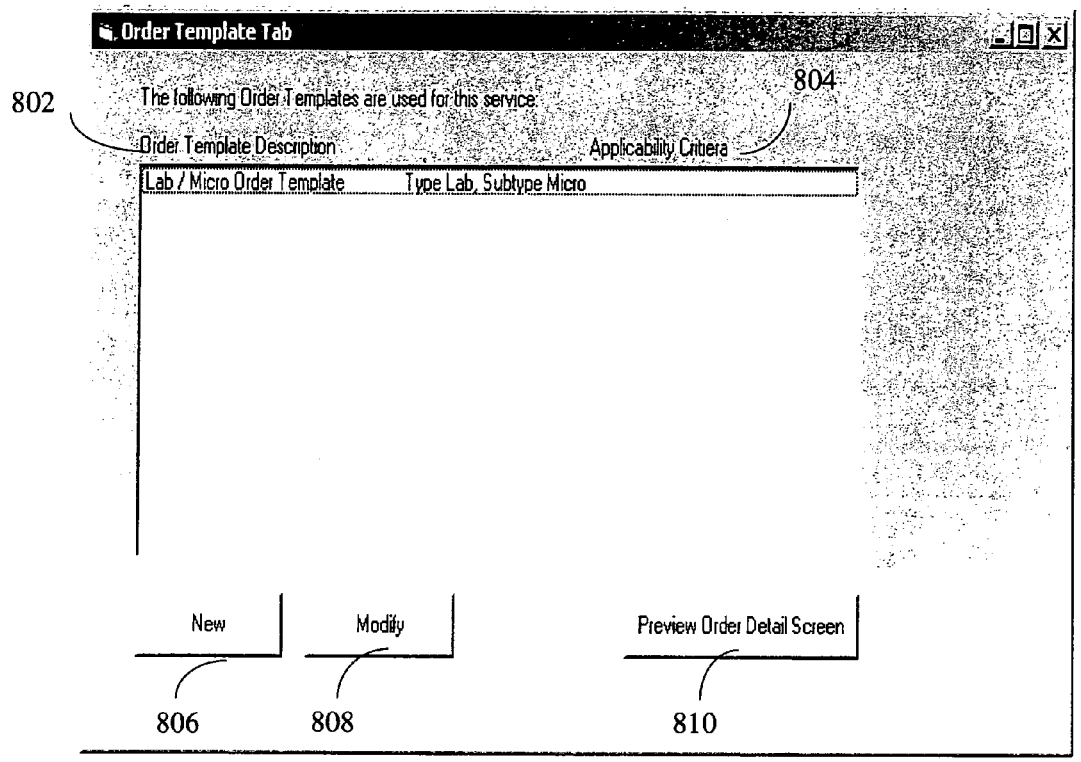
FIG. 8 illustrates an order template tab window based on the service catalog window, shown in FIG. 7, in accordance with a preferred embodiment of the present invention.

FIG. 8 illustrates an order template tab window 725 based on the service catalog window 700, shown in FIG. 7, in accordance with a preferred embodiment of the present invention. In particular, the order template tab window 725 generally includes an order template definition title 802, a criteria title 804, a new button 806, a modify button 808 and a preview order detail screen button 810. The order template tab window 725 permits the user to select and view predetermined order templates via the preview button 810, create new order templates via the new button 806, and modify an existing order template via the modify button 808.

Figure 9:
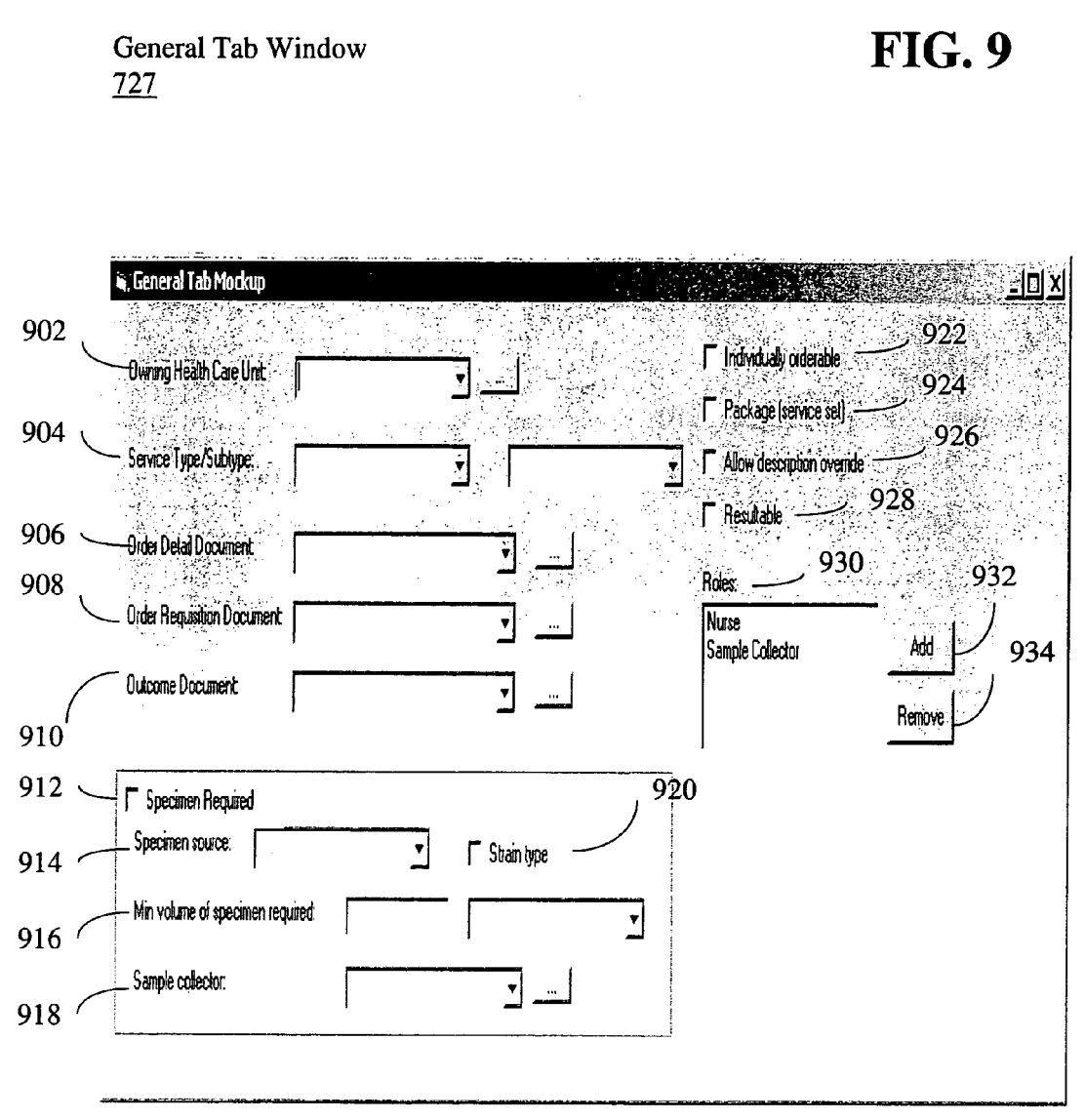

FIG. 9 illustrates a general tab window 727 based on the service catalog window 700, shown in FIG. 7, in accordance with a preferred embodiment of the present invention. The general tab window 727 generally includes a owning healthcare unit field 902, service type/subtype fields 904, an order detail document field 906, a order requisition document field 908, an outcome/result document field 910, a specimen required checkbox 912, a specimen source field 914, a minimum volume of specimen required field 916, a sample collector field 918, an individually operable checkbox 922, a package (service set) checkbox 924, an allow description override checkbox 926, a resultable checkbox 928, a roles field 930, an add checkbox 932, and a remove checkbox 934.

Figure 10:
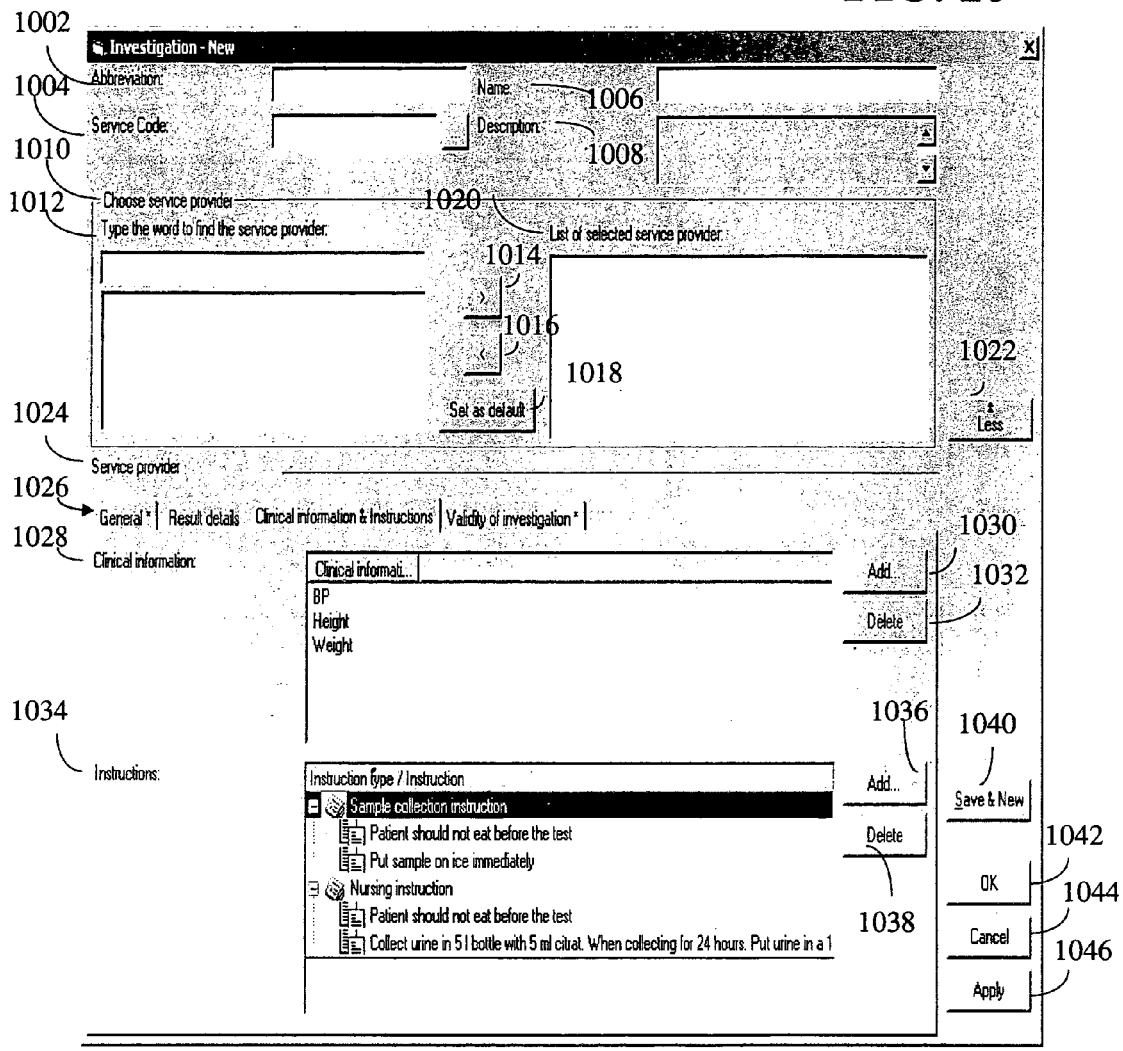
FIG. 10 illustrates an investigation window based on the service catalog window, shown in FIG. 7, in accordance with a preferred embodiment of the present invention.

FIG. 10 illustrates an investigation window 729 based on the service catalog window 700, shown in FIG. 7, in accordance with a preferred embodiment of the present invention. The investigation window 1000 generally includes an abbreviation field 1002, a service code field 1004, a name field 1006, a description field 1008, a choose service provider title 1010, a type word to find the service provider field 1012, a right arrow button 1014, a left arrow button 1016, a set as default button 1018, a list of selected service providers field 1020, a less button 1022, a service provider title 1024, several tabs 1026 including a general tab, a result details tab, a clinical information and instructions tab, a validity of investigation tab, and under the clinical information and instruction tab including clinical information field 1028, an add button 1030, a delete button 1032, an instructions field 1034, an add button 1036, a delete button 1038, a save and new button 1040, an ok button 1042, a cancel button 1044, and an apply button 1046.

The order detail screen flow varies based on the configuration definition for the specific service. The order generator 24 and/or 34 presents the order detail window 400 flow differently based on the following that are optionally defined in the service catalog window 700, under the general tab 727. Preferably, the order detail document field 906, the order requisition document field 908, and the outcome/result document field 910 are variable responsive to the service requesting/responsible healthcare unit and responsive to the specific service. The user may determine the format of the order form so that they can make it look more similar to a paper document layout or a data collection layout.

In particular, the order detail document 906 is an optional external document from clinical documentation used to present the document instead of visual basic (VB) detail form when it is valued. The order detail document 906 is associated with the service type/subtype fields 904 in FIG. 9. Alternatively, an order detail document may be acquired by selecting a template associated with a service in the order template tab window, as shown in FIG. 8. The order requisition document 908 is the clinical documentation template that, when valued, identifies that a clinical document needs to appear to collect additional detail information after the order detail form. For example, the MRI checklist clinical document may need to be displayed after the order detail form for the MRI appears. The outcome/result document 910 is the clinical documentation template that, when valued, identifies the specific outcome document to record outcome information that appears for the specific service in the outcome column in an activity planner module. Alternatively, rather than differentiating between the clinical documentation and the VB form, a web based system may be implemented.

In particular, the roles field identifies the security user roles associated to a service. This information is used by work list processing to be able to view a work list of requested services for a specific role. For example, the activity limit, bed rest service may be defined with a role of nursing. The nurse should be able to view the requested services work list and see services including this one that are specific to their role. They can also further limit the work list by the specific healthcare unit.

Referring back to FIG. 6, the method starts at step 601.

At step 602, the user opens a service catalog window 700.

At step 603, the user selects one or more services, and/or creates one or more services in the service catalog window 700.

At step 604, the user selects an order template by opening the order template from the service catalog window 700 under the order template tab 725.

At step 605, the user determines whether the existing order template is acceptable. If the existing order template is not acceptable, then the method continues to step 606. If the existing order template is acceptable, then the method continues to step 607.

Preferably, the user views the order templates 802 associated with the service under the order template tab 725. The criteria 804 for the order template 802 are also listed for the user's reference, without having to open the order template. Preferably, the system administrator should not need to redefine the order templates, but only view those already associated with the service if they were already defined by using order template editor window 300.

Preferably, when the user uses the order template editor first, then the service catalog window 700 would automatically show the order templates associated with the service when the user is doing maintenance. The service catalog and/or the order template editor may display the default order templates, depending on various design considerations. Preferably, the system administrator should not need to manually associate templates to services in the service catalog, and the system administrator should easily view (e.g., for troubleshooting) for a service the order templates that are to be applied based on the various criteria 308.

Preferably, the user can select to preview the order detail window 400 via the preview button 810 to view what the detail order form would look like when using the order templates. The user may select, add, or modify an order template using the order template editor window 300.

At step 606, the user creates a new order template from the service catalog window 700 using the order template editor window 300.

At step 607, the user assigns an existing or new order template to one or more, existing or new services from the service catalog window 700.

At step 608, the method ends.

Figure 11:
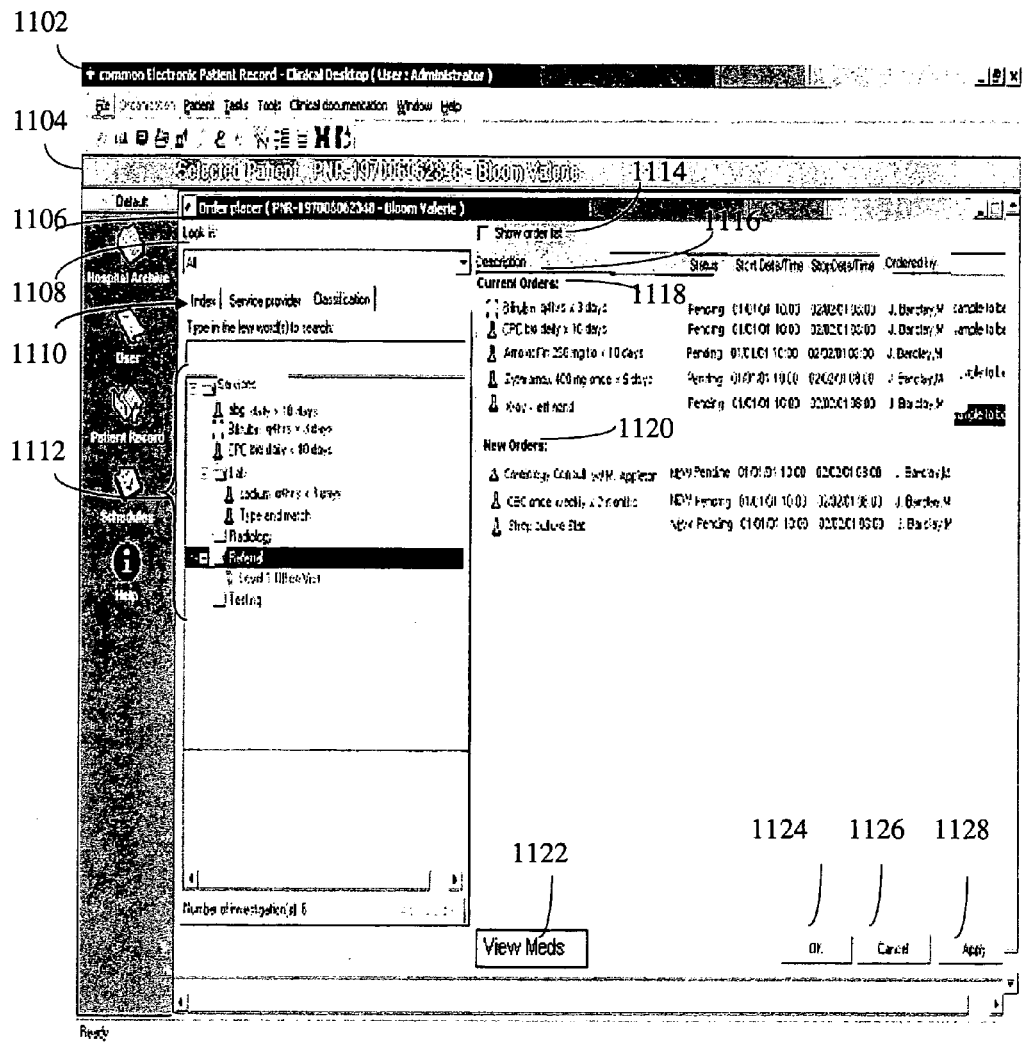
FIG. 11 illustrates an order placer window using the order generator, shown in FIG. 1, in accordance with a preferred embodiment of the present invention.

FIG. 11 illustrates an order placer window 1100 using the order generator 24 and/or 34, shown in FIG. 1, in accordance with a preferred embodiment of the present invention. The order placer window 1100 generally includes a patient record application title 1102, a selected patient application title 1104, an order placer application title 1106, a look in field 1108, several tabs 1110 including an index tab, a service provider tab, and a classification tab that includes a search field and services with summary descriptions 1112, a show order test 1114, a description label 1116 for current orders 1118 and new orders 1120, a view medicines button 1122, an ok button 1124, a cancel button 1126, and an apply button 1128. The order placer window 1100 permits a user to search for and select current or new orders.

FIG. 12 illustrates an order form window 1200 using the order placer window 1100, shown in FIG. 11, in accordance with a preferred embodiment of the present invention. The patient record application title 1102, the selected patient application title 1104, the order placer application title 1106 are the same elements as shown in FIG. 11. The order form window 1200 overlays one or more of these elements and displays the actual order form, as it would be printed in a paper format.

Preferably, inter-module dependencies exist among various clinical documentation modules implemented in the healthcare information system 10. For example, the features of the order generator are dependent on a clinical documentation builder module, otherwise called an adaptability tool that also generates other types of documents. Other types of templates include, without limitation, results, lab requisitions, assessments, problems, and any other template that may be related to the delivery of healthcare services to a patient. For example, the results template is another example of template that may be designed using a similar process and apparatus described above for integration with the service catalog. The results template provides a data driven process to generate a form presenting the results of a test or procedure, for example. Hence, any type of template may be used to generate any type of form, according to the process and apparatus disclosed herein. Hence, the terms "order generator," "order template," "order details," and "order form," as disclosed and claimed herein are intended to represent any type of generator, any type of template, any type of detail window, and any type of detailed form, respectively.

The various types of templates may include one or more of the following features. Templates may be created, modified, or copied. Templates are preferably activated or inactivated/deactivated in a similar manner as with the services for the order template. The ability to mark something as obsolete can be accomplished by inactivate/deactivating the template. The printed output may be different than what is visually presented on the detail form. Printed outputs may be printed on demand, automatically based on the function, or prompted by the user's selection from a list. The detail form may appear like a typical data collection screen or like a document format. Static headers and footers are not required, but are preferably standard and consistent across various applications as to what patient identification is shown on any detail form. The user preferably defines types and subtypes of services via the service type/subtype catalog. Data driven definition of parameters preferably supports all reporting requirements. Processing fields (e.g., duplicate check indicators, etc.) remain as a separate tab in the service catalog window 700. Preferably, the values, defaults, and allowable values of one parameter are conditionally related to one or more other parameter. Preferably, an instruction catalog has types of text that is reusable and typed (e.g., patient instructions, ancillary instructions, instructions to lab, etc.) These instructions are associated with services to permit default instructions when placing the order. Preferably, the default instructions are reusable across templates, and are part of the service catalog. Preferably, the system 10 has a default timeframe to retrieve clinical info (e.g., LMP date within last 12 hr shift). Preferably, the user may define and configuration columns for presentation on the display. The templates may also employ conditional prompting of questions (e.g., if an answer to a smoker question is yes, then additional questions will be presented related to how long, any lung cancer, etc.). Hence, the various types of template may share these, as well as other features.

In the windows displayed in FIGS. 3, 4, 7, 8, 9, 10, 11, and 12, each of the sections and the individual elements of the sections may be located at any place in the window and should not be limited to the particular located represented in the figures. Further, each of the sections and the individual elements of the sections may be implemented in various similar ways, to achieve the same result, which are well known in the art to those that design user interfaces. For example, the user may enter a command using a manual entry, a drop down window, an icon, a predetermined list, or voice recognition via a microphone, and the like. Further, for example, the information may be presented to the user using a display, having windows, files, text, graphics, images, charts, or lists, and the like, or using voice generation via a speaker.

The order generator 24 and/or 34 may be implemented using any type of software program language, including without limitation, visual basic, micro-code, C-code, and hyper-text language markup (HTML). Preferably, the software program language is HTML, resulting in a web-based application.

In brief summary of the preferred embodiment of the present invention, the order generator 24 and/or 34 provides the ability for the information defined by the system administrator in the service master file and other master files to define the service information to drive the form and content of the order to the end user in a dynamic fashion. These concepts are also referred to data driven because the data defined by the system administrator drives what is collected, validated against, etc. Specifically, the data driven concept includes the ability to vary definitional information responsive to such factors as the medically responsible organization for the patient, type of service, subtype of service, and for specific services, and other criteria. The order generator 24 and/or 34 dynamically creates the order form based on the master file definition by automatically placing the fields on the detail form based on their sequence identified. Additionally, the order generator 24 and/or 34 allows the system administrator the option of previewing and customizing the system generated form to make it aesthetically pleasing (e.g., frame captions, positioning, etc.). The system administrator can also define additional documentation templates required for certain types of orders that are not part of the basic required order and related clinical information, but are needed as support documentation. The document templates are accessible for quick access from the order detail form. During the order entry process, depending on the type, subtype of order, and specific service, the order generator 24 and/or 34 presents order and related clinical information to the user on the appropriate order detail form based on the information defined in the master files. The user views a list of related document templates for requisition details (e.g., MRI checklist for an MRI order) that the user may optionally select to fill out from the order entry flow.

Hence, while the present invention has been described with reference to various illustrative embodiments thereof, the present invention is not intended that the invention be limited to these specific embodiments. For example, the architectures, windows, menus, and processes presented in FIGS. 1-12 are not exclusive. Other architectures, windows, menus, and processes may also be derived in accordance with the principles of the invention to accomplish the same objectives. Further, the inventive principles may be advantageously employed in any activity planner system and is not limited to use in the healthcare field. Those skilled in the art will recognize that variations, modifications, and combinations of the disclosed subject matter can be made without departing from the spirit and scope of the invention as set forth in the appended claims.

What is claimed is:

1. A computer implemented automated method for providing a form for display to a user for ordering particular services supporting healthcare delivery to a patient, comprising the steps of:
acquiring data identifying order types and associated parameter types;
automatically analyzing said acquired data to provide collated data suitable for presentation in a display form for use in placing an order for a particular type of service to be provided to a patient, said analyzing including parsing said acquired data to determine:
(a) type of display fields for incorporation in said display form,
(b) a sequence of presentation of said display fields in said display form, and
(c) placement of said display fields in said display form; and
automatically processing said collated data to prepare data, representing said display form, for use in placing said order for said particular type of service to be provided to a patient and presenting a user with allowable values for a parameter associated with a particular order type for said particular type of service by deriving said allowable values from memory.

2. A method according to claim 1,
wherein said acquiring step includes the step of:
acquiring parameter definition elements associated with an individual parameter type, and wherein said analyzing step includes the step of:
incorporating a first parameter definition element associated with a first parameter type when an order is placed within a first healthcare organization department, and incorporating a second parameter definition element associated with a second parameter type when an order is placed within a different, second healthcare organization department.

3. A method according to claim 2, wherein
said parameter definition elements comprise at least one of,
(a) parameter values, (b) a parameter qualifier identifying characteristics of an ordered service, (c) a parameter qualifier identifying a required delivery priority of an ordered service, (d) a parameter qualifier identifying delivery requirements of an ordered service, and (e) a parameter qualifier identifying means of delivery of an ordered service.

4. A method according to claim 2, wherein
at least one of said first and second healthcare organization departments further comprises at least one of: (a) a hospital unit, (b) a laboratory, (c) a pharmacy, (d) administration, (e) an outpatient unit, (f) an inpatient unit, (g) an imaging unit, and (h) a clinical unit.

5. A method according to claim 1, further comprising the step of:
sequencing presentation of said display fields in said display form in order from left to right and from top to bottom.

6. A method according to claim 1, wherein
said service further comprises at least of: (a) an order for goods for the patient, and (b) an order for a service to be performed for the patient.

7. A method according to claim 1, wherein said step of acquiring data identifying order types and associated parameter types further comprises:
receiving data entered using a template form for determining characteristics of said display form for use in placing the order for the particular type of service.

8. An order form generator for a healthcare information system comprising:
a user interface including:
an input device adapted to receive input information related to format and content of an order form for a patient for ordering a particular type of service to be provided to a patient; and
a display adapted to present the input information and output information related to the order form, wherein the display includes:
an order template editor window adapted to permit a user to initiate generation of an order template responsive to receiving the input information, and
an order details window adapted to permit the user to initiate generation of the order form responsive to a generated order template; and
a processor adapted to automatically generate the order form using a generated order template responsive to receiving the input information by automatically processing said input information related to format and content of an order form to prepare data, representing said display form, for use in placing said order for said particular type of service to be provided to a patient and presenting a user with allowable values for a parameter associated with a particular order type for said particular type of service by deriving said allowable values from memory.

9. An order generator according to claim 8, wherein the display further includes:
a service catalog window adapted to permit the user to assign a service to the order template.

10. An order generator according to claim 9, wherein the display further includes:
an order template tab window adapted to permit the user to select an order template assigned to the service.

11. An order generator according to claim 9, wherein the display further includes:
a general tab window adapted to permit the user to provide information related to the service.

12. An order generator according to claim 9, wherein the display further includes:
an investigation window adapted to permit the user to provide instruction information related to the service.

13. An order generator according to claim 8, wherein the display further includes:
an order placer window adapted to permit the user to search for and select the order form.

14. An order generator according to claim 13, wherein the display further includes:
an order form window adapted to display the order form to the user.

15. An order generator according to claim 8, wherein the order template editor window further comprises at least one of:
at least one order template criteria related to the at least one order template, at least one parameter related to the at least one order template, and characteristics related to the at least one parameter.

16. A computer implemented method for providing a form for display to a user for ordering particular services supporting healthcare delivery to a patient, comprising the steps of:
acquiring data identifying order types and associated parameter types;
automatically analyzing said acquired data to provide collated data suitable for presentation in a display form for use in placing an order for a particular type of service to be provided to a patient, said analyzing including parsing said acquired data to determine:
(a) type of display fields for incorporation in said display form,
(b) a sequence of presentation of said display fields in said display form, and
(c) placement of said display fields in said display form; and adaptively selecting display fields for incorporation in data representing said display form for use in placing said order for said particular type of service to be provided to a patient in response to information identifying a source of said order, said display fields including a field for presenting a user with allowable values for a parameter associated with said order for said particular type of service by deriving said allowable values from memory.

17. A method according to claim 16, wherein said information identifying a source of said order further comprises at least one of: (a) user identification information, (b) information identifying an organization affiliated with a user, (c) user entered information identifying an organization to be associated with said order, (d) user location identification information and (e) information identifying a workflow task sequence associated with said order.

* * * * *